(12) United States Patent
Allmendinger et al.

(10) Patent No.: US 7,115,777 B2
(45) Date of Patent: Oct. 3, 2006

(54) AMIDE DERIVATIVES AS INHIBITORS OF THE ENZYMATIC ACTIVITY OF RENIN

(75) Inventors: Thomas Allmendinger, Lörrach (DE); Peter Furter, Binningen (CH)

(73) Assignee: Novartis AG, Basel (CH)

( * ) Notice: Subject to any disclaimer, the term of this patent is extended or adjusted under 35 U.S.C. 154(b) by 53 days.

(21) Appl. No.: 10/516,054

(22) PCT Filed: May 28, 2003

(86) PCT No.: PCT/EP03/05635

§ 371 (c)(1),
(2), (4) Date: Feb. 14, 2005

(87) PCT Pub. No.: WO03/099767

PCT Pub. Date: Dec. 4, 2003

(65) Prior Publication Data

US 2005/0234126 A1 Oct. 20, 2005

(30) Foreign Application Priority Data

May 29, 2002 (GB) .................... 0212410.5

(51) Int. Cl.
*C07C 233/05* (2006.01)
*C07D 263/04* (2006.01)
*A61K 31/16* (2006.01)
*A61K 31/415* (2006.01)

(52) U.S. Cl. ............... 564/153; 548/229; 514/386; 514/616

(58) Field of Classification Search ............. 514/386, 514/616; 564/153; 548/229
See application file for complete search history.

(56) References Cited

U.S. PATENT DOCUMENTS

| | | | |
|---|---|---|---|
| 5,559,111 A | 9/1996 | Göschke et al. | 514/227.5 |
| 5,606,078 A | 2/1997 | Göschke et al. | 549/321 |
| 5,627,182 A | 5/1997 | Göschke et al. | 514/237.8 |
| 5,646,143 A | 7/1997 | Göschke et al. | 514/233.8 |
| 5,654,445 A | 8/1997 | Göschke et al. | 549/321 |
| 5,659,065 A | 8/1997 | Göschke | 560/29 |
| 5,705,658 A | 1/1998 | Göschke et al. | 549/321 |
| 6,670,507 B1 * | 12/2003 | Bellus et al. | 564/134 |

FOREIGN PATENT DOCUMENTS

EP 0 678 503 B1 10/1995
WO WO 02/40007 5/2002

OTHER PUBLICATIONS

Dondoni et al, Tetrahedron Letters, 42, 2001, 4819-4823.*

* cited by examiner

*Primary Examiner*—Shailendra Kumar
(74) *Attorney, Agent, or Firm*—Gregory Ferraro

(57) ABSTRACT

The present inventions relates to a novel compound of formula (I)

or a pharmaceutically acceptable salt thereof, the use and manufacture of a compound of formula (I) or a pharmaceutical composition comprising a compound of formula (I).

15 Claims, No Drawings

AMIDE DERIVATIVES AS INHIBITORS OF THE ENZYMATIC ACTIVITY OF RENIN

This application is a 371 of PCT/EP03/05635, filed May 28, 2003.

The present inventions relates to a novel compound of formula (I)

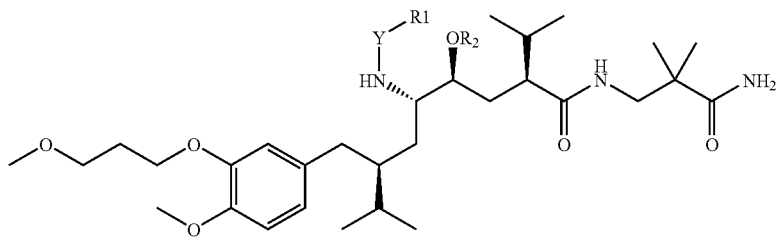

or a pharmaceutically acceptable salt thereof;
wherein Y represents the group —C(=X) or $SO_2$; and
(i) $R_1$ and $R_2$ together form a single bond or methylene; and, if Y represents the group —C(=X), X represents NH, S, or O; or
(ii) $R_1$ represents $C_1$–$C_7$-alkyl; or represents $C_1$–$C_7$alkyl that is substituted by a substituent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; or represents $C_1$–$C_7$-alkoxy that is unsubstituted or substituted by a substiuent selected from the group consisting of $C_1$–$C_7$-alkyl, $C_1$–$C_7$-alkoxy, hydroxy, halogen, $CF_3$, nitro and cyano; and $R_2$ represents hydrogen; and, if Y represents the group —C(=X), X represents NH, S, or O; or
(iii) $R_1$ represents amino; $R_2$ represents hydrogen; and, if Y represents the group —C(=X), X represents NH; or wherein Y represents the group —C(=X); and
(iv) $R_1$ and $R_2$ together form a the group —CO—O—; and X represents O;
the use and manufacture of a compound of formula (I) or a pharmaceutical composition comprising a compound of formula (I).

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula (I).

The compounds of formula (I) may be present in the form of salts, in particular pharmaceutically acceptable salts. In each case, acid addition salts may be formed with the basic amino group. Suitable acid components are for example strong inorganic acids, such as mineral acids, for example halogen halides, e.g. hydrochloric acid, or strong organic carboxylic acids, for example acetic acid or trifluoroacetic acid, or organic sulfonic acids, e.g. methanesulfonic acid or p-toluenesulfonic acid. In a broader sense, the invention relates also to salts which are not suitable for therapeutic purposes and may be used for example in the isolation or purification of free compounds of formula (I) or pharmaceutically acceptable salts thereof. Only salts that are pharmaceutically acceptable and non-toxic are used therapeutically and those salts are therefore preferred.

The general terms used hereinbefore and hereinafter have the following meanings, unless defined otherwise.

$C_1$–$C_7$-Alkyl is for example methyl, ethyl, n-propyl, isopropyl, n-butyl, isobutyl, sec-butyl, tert-butyl or a corresponding pentyl, hexyl or heptyl radical. $C_1$–$C_4$-alkyl, especially methyl and ethyl, is preferred.

$C_1$–$C_7$-Alkyl that is substituted by amino represents in particular amino-$C_1$–$C_4$-alkyl, especially aminomethyl, 1- or 2-aminoethyl, or 2-amino-3-methyl-propyl.

$C_1$–$C_7$-Alkyl that is substituted by carboxy represents in particular carboxy-$C_1$–$C_4$-alkyl, especially 3-carboxy-propyl.

$C_1$–$C_7$-Alkyl that is substituted by amino and carboxy represents in particular $C_1$–$C_4$-alkyl that is substituted by amino and carboxy, especially 3-amino-3-carboxy-propyl (including the racemic form as well as the (S)- and (R)-enantiomer thereof).

Hydroxy-$C_1$–$C_7$-alkyl-amino represents in particular hydroxy-$C_1$–$C_4$-alkyl-amino, especially 2-hydroxy-ethylamino.

$C_1$–$C_7$-alkoxy-$C_1$–$C_7$-alkyl-amino represents in particular $C_1$–$C_4$-alkoxy-$C_1$–$C_4$-alkyl-amino, especially 2-methoxy-ethylamino-methyl.

Aryl (that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano) represents in particular phenyl or naphthyl such as 2- or 3-naphthyl, or biphenylyl such as 2-, 3- or 4-biphenylyl. Aryl preferably is phenyl. Substituted aryl preferably is mono-, di- or trisubstituted. Preferred substituted aryl is phenyl that is mono-substituted by nitro such as 4-nitrophenyl or that is di-substituted by $C_1$–$C_7$-alkoxy and carboxy such as 3-ethoxy-4-carboxy-phenyl.

Halogen represents in particular halogen with an atomic number up to and including 35, i.e. fluorine, chlorine or bromine, and in a broader sense includes iodine. Fluorine or chlorine is preferred.

$C_1$–$C_7$-Alkoxy that is unsubstituted or substituted by a substiuent selected from the group consisting of $C_1$–$C_7$-alkyl, $C_1$–$C_7$-alkoxy, hydroxy, halogen, $CF_3$, nitro and cyano represents in particular $C_1$–$C_4$-alkoxy that is unsubstituted or substituted by a substiuent selected from the group consisting of $C_1$–$C_4$-alkyl, $C_1$–$C_4$-alkoxy, hydroxy, halogen, $CF_3$, nitro and cyano. Preferred substituted alkyl is, for example, Ethoxy-methyl, 2-Ethoxy-ethyl, hydroxymethyl, 2-hydroxy-ethyl, chloromethyl, 2-chloroethyl, trifluoromethyl, trichloromethyl, nitromethyl or cyanomethyl.

The compounds of the present invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors is demonstrated inter alia experimentally by means of in vitro tests, the reduction in the formation of angiotensin I being measured in various systems (human plasma, purified human renin together with synthetic or natural renin substrate). Inter alia the following in vitro test is used: an extract of human renin from the kidney (0.5 mGU [milli-Goldblatt units]/ml) is incubated for one hour at 37° C. and pH 7.2 in 1-molar aqueous 2-N-(tris-hydroxymethyl)-amino-ethane-sulfonic acid buffer solution with 23 μg/ml of synthetic renin substrate, the tetradecapeptide H-Asp-Arg-Val-Tyr-Ile-His-Pro-Phe-His-Leu-Leu-Val-Tyr-Ser-OH. The amount of angiotensin I formed is determined by radioimmunoassay. Each of the inhibitors according to the invention is added to the incubation mixture at different concentrations. The $IC_{50}$ is defined as the concentration of a particular inhibitor that reduces the formation of angiotensin I by 50%. In the in vitro systems the compounds of the present invention exhibit inhibiting activities at minimum concentrations of from approximately $10^{-6}$ to approximately $10^{-10}$ mol/l.

In animals deficient in salt, renin inhibitors bring about a reduction in blood pressure. Human renin differs from the renin of other species. In order to test inhibitors of human renin, primates (marmosets, *Callithrix jacchus*) are used, because human renin and primate renin are substantially homologous in the enzymatically active region. Inter alia the following in vivo test is used: the test compounds are tested on normotensive marmosets of both sexes having a body weight of approximately 350 g that are conscious, allowed to move freely and in their normal cages. The blood pressure and heart rate are measured via a catheter in the descending aorta and recorded radiometrically. The endogenous release of renin is stimulated by the combination of a 1-week low-salt diet and a single intramuscular injection of furosemide (5-(aminosulfonyl)- 4-chloro-2-[(2-furanyl-methyl)-amino]-benzoic acid) (5 mg/kg). 16 hours after the injection of furosemide the test compounds are administered either directly into the femoral artery using an injection cannula or, in the form of a suspension or solution, via an oesophageal tube into the stomach, and their action on the blood pressure and heart rate are evaluated. In the in vivo test described, the compounds of the present invention have hypotensive action at doses of from approximately 0.001 to approximately 0.3 mg/kg i.v. and at doses of from approximately 0.01 to approximately 30 mg/kg p.o.

The compounds of the present invention also have the property of regulating, especially reducing, intra-ocular pressure.

The extent of the reduction in intra-ocular pressure after administration of a pharmaceutical active ingredient of formula (I) according to the present invention can be determined, for example, in animals, for example rabbits or monkeys. Two typical experimental procedures that illustrate the present invention, but are not intended to limit it in any way, are described hereinafter.

The in vivo test on a rabbit of the "Fauve de Bourgogne" type to determine the intra-ocular-pressure-reducing activity of topically applied compositions can be designed, for example, as follows. The intra-ocular pressure (IOP) is measured using an aplanation tonometer both before the experiment and at regular intervals of time. After a local anaesthetic has been administered, the suitably formulated test compound is applied topically in a precisely defined concentration (e.g. 0.000001–5% by weight) to one eye of the animal in question. The contralateral eye is treated, for example, with physiological saline. The measured values thus obtained are evaluated statistically.

The in vivo tests on monkeys of the species *Macaca Fascicularis* to determine the intra-ocular-pressure-reducing activity of topically applied compositions can be carried out, for example, as follows. The suitably formulated test compound is applied in a precisely defined concentration (e.g. 0.000001–5% by weight) to one eye of each monkey. The other eye of the monkey is treated correspondingly, for example with physiological saline. Before the start of the test the animals are anaesthetsed with intramuscular injections of, for example, ketamine. At regular intervals of time, the intra-ocular pressure (IOP) is measured. The test is carried out and evaluated in accordance with the rules of "good laboratory practice" (GLP).

The compounds of the present invention can be used in the treatment of hypertension, congestive heart failure, cardiac hypertrophy, cardiac fibrosis, cardiomyopathy postinfarction, complications resulting from diabetes, such as nephropathy, vasculopathy and neuropathy, diseases of the coronary vessels, restenosis following angioplasty, raised intra-ocular pressure, glaucoma, abnormal vascular growth, hyperaldosteronism, anxiety states and cognitive disorders.

The groups of compounds mentioned below are not to be regarded as exclusive; rather, for example in order to replace general definitions with more specific definitions, parts of those groups of compounds can be interchanged or exchanged for the definitions given above, or omitted, as appropriate.

Preferred Y is —C(=X)—. Preferred $R_1$ is $C_1$–$C_7$-alkyl and preferred $R_2$ is hydrogen. Likewise preferred is where $R_1$ and $R_2$ together form the group —CO—O—. Preferred X is O.

The invention relates to a compound of formula (I A)

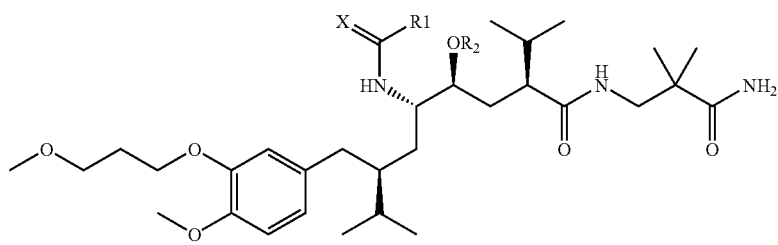

or a pharmaceutically acceptable salt thereof, wherein
(i) $R_1$ and $R_2$ together form a single bond or methylene; and X represents NH, S, or O; or
(ii) $R_1$ represents $C_1$–$C_7$-alkyl; or represents $C_1$–$C_7$-alkyl that is substituted by a substitutent selected from the group consisting of amino, carboxy, hydroxy-$C_1$–$C_7$-alkyl-amino, $C_1$–$C_7$ alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; or represents $C_1$–$C_7$-alkoxy that is unsubstituted or substituted by a substiuen selected from the group consisting of $C_1$–$C_7$-alkyl, $C_1$–$C_7$-alkoxy, hydroxy, halogen, $CF_3$, nitro and cyano; and $R_2$ represents hydrogen; and X represents NH, S, or O; or
(iii) $R_1$ represents amino; $R_2$ represents hydrogen; and X represents NH.;

The invention relates especially to a compound of formula (I), Y represents $SO_2$, and $R_1$ represents $C_1$–$C_7$-alkyl; or represents $C_1$–$C_7$-alkyl that is substituted by a substituent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; or represents $C_1$–$C_7$-alkoxy that is unsubstituted or substituted by a substiuent selected from the group consisting of $C_1$–$C_7$-alkyl, $C_1$–$C_7$-alkoxy, hydroxy, halogen, $CF_3$, nitro and cyano; and $R_2$ represents hydrogen; or a pharmaceutically acceptable salt thereof.

The invention relates especially to a compound of formula (I) or (I A), respectively, wherein Y is $SO_2$ or C(=X)—; $R_1$ and $R_2$ together form a single bond; and X represents NH, S, or especially O, or a pharmaceutically acceptable salt thereof.

The invention relates especially to a compound of formula (I A), wherein $R_1$ and $R_2$ together form a single bond and X is O; or a pharmaceutically acceptable salt thereof.

The invention relates especially to a compound of formula (I A), wherein $R_1$ represents a residue selected from the group consisting of $C_1$–$C_4$-alkyl, $C_1$–$C_4$-alkoxy or aryl, for example, phenyl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; $R_2$ is hydrogen; and X is O;

or a pharmaceutically acceptable salt thereof.

The invention relates especially to a compound of formula (I A), wherein $R_1$ represents $C_1$–$C_4$-alkyl; $R_2$ is hydrogen; and X is O;

or a pharmaceutically acceptable salt thereof.

The invention relates specifically to the compounds of formula I mentioned in the Examples and to the salts thereof, especially the pharmaceutically acceptable salts thereof.

The compounds of formula (I) or pharmaceutically acceptable salts thereof can be prepared according to methods which are known per se by the person skilled in the pertinent art.

The present invention also relates to the manufacture of a compound of formula (I) or a salt thereof, wherein Y represents $SO_2$, and $R_1$ represents $C_1$–$C_7$-alkyl; or represents $C_1$–$C_7$-alkyl that is substituted by a substitutent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; or represents $C_1$–$C_7$-alkoxy that is unsubstituted or substituted by a substiuent selected from the group consisting of $C_1$–$C_7$-alkyl, $C_1$–$C_7$-alkoxy, hydroxy, halogen, $CF_3$, nitro and cyano; and $R_2$ represents hydrogen; comprising (a) acylating a compound of formula

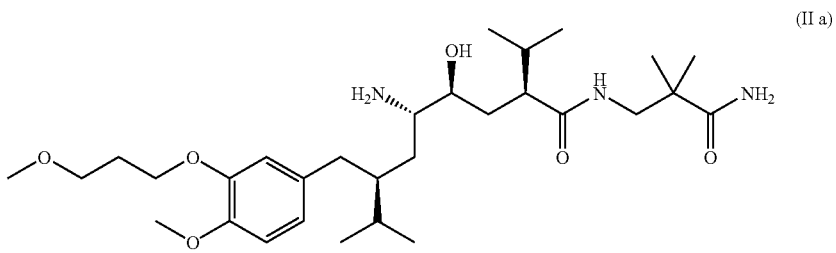

(II a)

chemically defined as 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide (generic name: aliskiren), specifically disclosed in EP 678503 A, with a compound of formula $R_1$—$SO_2$-Hal (II b), wherein Hal is halogen, especially chloro or bromo; and (b) isolating a compound of formula (I) or a salt thereof.

The reaction is, for example, carried out in the presence of a suitable base. Suitable bases are, for example, alkali metal hydroxides, hydrides, amides, alkanolates, carbonates, hydrogencarbonates, triphenylmethylides, tri-lower alkylamides, aminoalkylamides or lower alkylsilylamides, naphthaleneamines, lower alkylamines, basic heterocycles, ammonium hydroxides, and carbocyclic amines. Examples which may be mentioned are sodium hydroxide, sodium hydride, sodium amide, sodium methoxide, sodium ethoxide, potassium tert-butoxide, potassium carbonate, sodium hydrogencarbonate, lithium triphenylmethylide, lithium diisopropylamide, potassium 3-(aminopropyl)amide, potassium bis(trimethylsilyl)-amide, dimethylaminonaphtha(ene, di- or triethylamine, or ethyldiisopropylamine, N-methylpiperidine, pyridine, benzyltrimethylammonium hydroxide, 1,5-diazabicyclo[4.3.0]non-5-ene (DBN) and 1,8-diaza-bicyclo[5.4.0]undec-7-ene (DBU). If an acid anhydride of formula (II b) is used sodium hydrogencarbonate is preferably used as base.

The present invention also relates to the manufacture of a compound of formula (I) or a salt thereof, wherein Y represents the group —C(═X); $R_1$ and $R_2$ together form a single bond or methylene; and X represents NH, S, or O; comprising (a) N-acylating a compound of formula

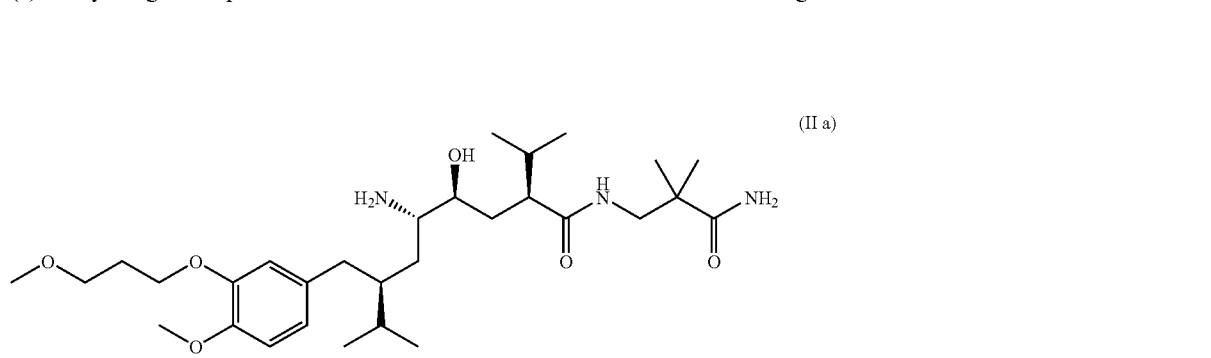

(II a)

with carbonyldiimidazole and (b) isolating a compound of formula (I) or a salt thereof.

The reaction is, for example, carried out in the presence of a suitable base. Suitable bases are, for example, those that are described above.

The present invention also relates to the manufacture of a compound of formula (I) or a salt thereof, wherein Y represents the group —C(═X); $R_1$ represents $C_1$–$C_7$-alkyl; or represents $C_1$–$C_7$-alkyl that is substituted by a substituent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substituent selected from the group consisting of $C_1$–$C_7$-alkyl, $C_1$–$C_7$-alkoxy, hydroxy, carboxy, halogen, $CF_3$, nitro and cyano; or represents $C_1$–$C_7$ alkoxy that is unsubstituted or substituted by a substituent selected from the group consisting of $C_1$–$C_7$-alkyl, $C_1$–$C_7$alkoxy, hydroxy, halogen, $CF_3$, nitro and cyano; and $R_2$ represents hydrogen; and X represents NH, O or S; comprising (a) treating a compound of formula (II a) with a reactive compound of formula (II c) Z-C(═X)—$R_1$, wherein Z represents halogen or a residue of formula $R_1$—C(═X)—O— or is hydroxy; in the presence of a condensation agent and (b) isolating the resulting compound of formula (I) or a salt thereof.

X in a compound of formula (II c) is preferably O.

The reaction is, for example, carried out in the presence of a suitable base. Suitable bases are, for example, those that are described above.

The reaction may also be carried out, if suitable, in the presence of a customary condensation agent, especially, if Z is hydroxy. Said agent is, for example, a carbodiimide, for example diethyl-, dipropyl-, N-ethyl-N'-(3-dimethylaminopropyl)-carbodiimide or especially dicyclohexyl-carbodiimide, also a suitable carbonyl compound, for example carbonyl-dilmidazole, a 1,2-oxazolium compound, for example 2-ethyl-5-phenyl-1,2-oxazolium-3'-sulfonate and 2-tert-butyl-5-methyl-isoxazolium perchlorate, or a suitable acylamino compound, for example 2-ethoxy-1-ethoxycarbonyl-1,2-dihydro-quinoline, also activated phosphoric acid derivatives, for example diphenylphosphoryl azide, diethyl-phosphoryl cyanide, phenyl-N-phenyl-phosphoroamidochloridate, bis(2-oxo-3-oxazolidinyl)-phosphinic acid chloride or 1-benzo-triazolyloxy-tris(dimethylamino)-phosphonium hexafluorophosphate.

Preferred halogen Z is chloro or bromo.

The present invention also relates to the manufacture of a compound of formula (I) or a salt thereof, wherein $R_1$ represents amino; $R_2$ represents hydrogen; and X represents NH; comprising (a) reacting a compound of formula (II a) or a salt thereof with $H_2N$—CN;

(b) isolating a compound of formula (I) or a salt thereof.

The reaction is carried out in a polar solvent, for example, water or an alkohol, such as an $C_1$–$C_4$-alkanol, or a mixture thereof. Preferably, the pH is adjusted to 1 to 10.

The present invention also relates to the manufacture of a compound of formula (I) or a salt thereof, wherein Y is —C(═X)—; $R_1$ and $R_2$ together form a the group —CO—O—; and X represents O; comprising (a) reacting a compound of formula (II a) or a salt thereof with an oxalic acid ester or anhydride or especially an oxalylhalide, especially an oxalylchloride or formula

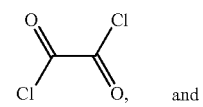

and (b) isolating a compound of formula (I) or a salt thereof.

The reaction is carried out in the presence of a suitable base. Suitable bases are, for example, those that are described above.

The reactions described hereinabove and hereinbelow are carried out in a manner known per se, for example in the absence or, usually, in the presence of a suitable solvent or diluent or a mixture thereof, the operation being carried out as necessary with cooling, at room temperature or with heating, for example in a temperature range of approximately from −80° C. to the boiling temperature of the reaction medium, especially from about −10° to about +200° C., and, if necessary, in a closed vessel, under pressure, in an inert gas atmosphere and/or under anhydrous conditions.

The process for the manufacture of a compound of formula (I) or a pharmaceutically acceptable salt thereof can, for example, be illustrated by following reaction scheme:

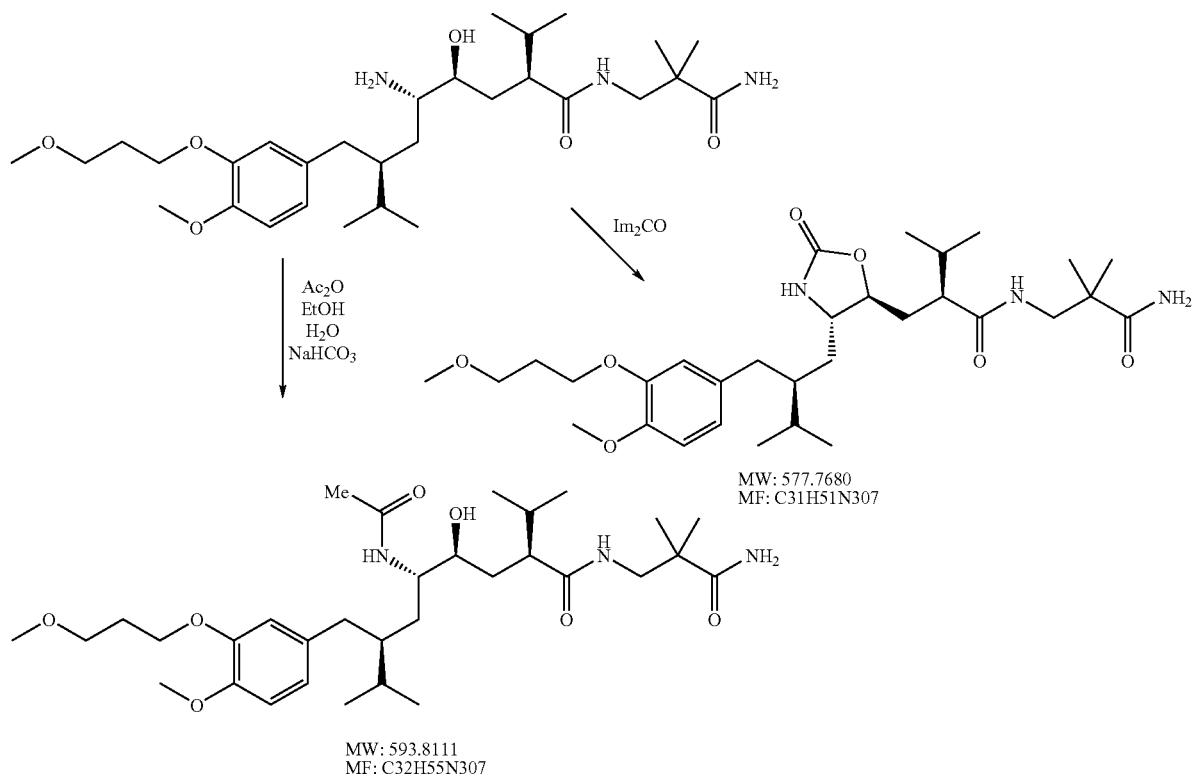

Im₂CO is carbonyidiimidazole.

The isolation steps of a compound of formula (I) or (I A), respectively, is carried out according to conventional isolation methods, such as by crystallizing the resulting compound of formula (I) or (I A), respectively, from the reaction mixture or by chromatography of the reaction mixture.

The invention is especially illustrated by the working examples and relates also to the novel compounds mentioned in the working examples and also to their use and to processes for their preparation.

The starting material of formulae (II a), (II b) and (II c) are either known or can be obtained following methods known per se. Compounds of formula (II a), for example, can be prepared following the methods as described in EP 678503.

Salts of compounds of formula (I) or (I A), respectively, can be prepared in a manner known per se. For example, acid addition salts of compounds of formula (I) or (I A), respectively, re obtained by treatment with an acid or a suitable ion exchange reagent. Acid addition salts can be converted into the free compounds in customary manner, e.g. by treatment with a suitable basic agent.

Resulting acid addition salts can be converted into other salts in a manner known per se, for example by treatment with a suitable metal salt, such as a sodium, barium or silver salt, of a different acid in a suitable solvent in which an inorganic salt formed is insoluble and is therefore eliminated from the reaction equilibrium.

The compounds of formula (I) or (I A), respectively, including a salt thereof, may also be obtained in the form of a hydrate or may include the solvent used for crystallisation (solvates).

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The invention especially relates to a combination, such as a combined preparation or pharmaceutical composition, respectively, comprising a compound of formula (I) or (I A), respectively, or a pharmaceutically acceptable salt thereof and at least one therapeutic agent selected from the group consisting of (i) an AT₁-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

The combination according to the present invention likewise comprises at least one pharmaceutically acceptable carrier.

The term "at least one therapeutic agent" shall mean that in addition to the compound of formula (I) one or more, for example two, furthermore three, active ingredients as specified according to the present invention can be combined.

$AT_1$-receptor antagonists (also called angiotensin II receptor antagonists) are understood to be those active ingredients that bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds that are selected from the group consisting of valsartan (cf. EP 443983), losartan (cf. EP253310), candesartan (cf. 459136), eprosartan (cf. EP 403159), irbesartan (cf. EP45451 1), olmesartan (cf. EP 503785), tasosartan (cf. EP539086), telmisartan (cf. EP 522314), the compound with the designation E-1477 of the following formula

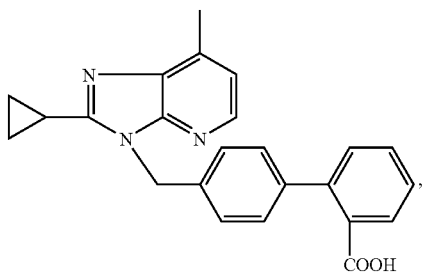

the compound with the designation SC-52458 of the following formula

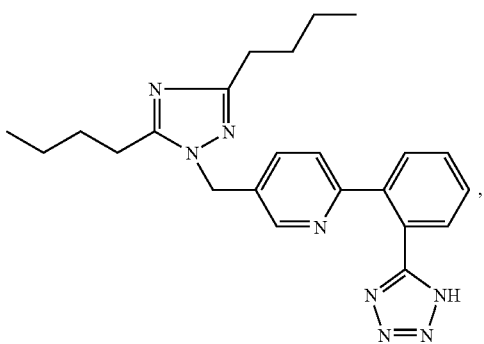

and the compound with the designation the compound ZD-8731 of the following formula

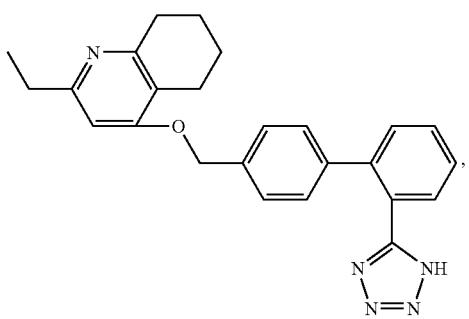

or, in each case, a pharmaceutically acceptable salt thereof.

Preferred $AT_1$-receptor antagonist are those agents that have been marketed, most preferred is valsartan or a pharmaceutically acceptable salt thereof.

The interruption of the enzymatic degradation of angiotensin I to angiotensin II with so-called ACE-inhibitors (also called angiotensin converting enzyme inhibitors) is a successful variant for the regulation of blood pressure and also a therapeutic method for the treatment of congestive heart failure.

The class of ACE inhibitors comprises compounds having differing structural features. For example, mention may be made of the compounds which are selected from the group consisting alacepril, benazepril, benazeprilat, captopril, ceronapril, cilazapril, delapril, enalapril, enalaprilat, fosinopril, imidapril, lisinopril, moexipril, moveltopril, perindopril, quinapril, quinaprilat, ramipril, ramiprilat, spirapril, temocapril, trandolapril and zofenopril, or, in each case, a pharmaceutically acceptable salt thereof.

Preferred ACE inhibitors are those agents that have been marketed, most preferred are benazepril, enalapril, lisinopril and especially ramipril.

A beta blocker in said combination preferably is a representative selected from the group consisting of a selective β1-blocker, such as atenolol, bisoprolol (especially the fumarate thereof), metoprolol (especilily the hemi-(R,R) fumarate or fumarate thereof), furthermore, acetutolol (especially the hydrochloride thereof), esmolol (especially the hydrochloride thereof), celiproplol (especially the hydrochloride thereof), taliprolol, or acebutolol (especially the hydrochloride thereof), a non-selective β-blocker, such as oxprenolol (especially the hydrochloride thereof), pindolol, furthermore, propanolol (especially the hydrochloride thereof), bupranolol (especially the hydrochloride thereof), penbutolol (especially the sulphate thereof), mepindolol (especially the sulphate thereof), carteolol (especially the hydrochloride thereof) or nadolol, and a β-blocker with α-blocking activity such as carvedilol; or in each case, a pharmaceutically acceptable salt thereof.

The class of calcium channel blockers (CCBs) essentially comprises dihydropyridines (DHPs) and non-DHPs such as dilitiazem-type and verapamil-type CCBs. A CCB useful in said combination is preferably a DHP representative selected from the group consisting of amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs. Preferred CCBs comprise amlodipine, diltiazem, isradipine, nicardipine, nifedipine, nimodipine, nisoldipine, nitrendipine, and verapamil, or, e.g. dependent on the specific CCB, a pharmaceutically acceptable salt thereof. Especially preferred as DHP is amlodipine or a pharmaceutically acceptable salt, especially the besylate thereof, furthermore the maleate, thereof. An especially preferred representative of non-DHPs is verapamil or a pharmaceutically acceptable salt, especially the hydrochloride, thereof.

Aldosterone synthase is an enzyme that converts corticosterone to aldosterone by hydroxylating corticosterone to form 18-OH-corticosterone and 18-OH-corticosterone to aldosterone. The class of aldosterone synthase inhibitors is known to be applied for the treatment of hypertension and primary aldosteronism comprises both steroidal and non-steroidal aidosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of anastrozole, fadrozole (including the (+)-enantiomer thereof), as well as exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

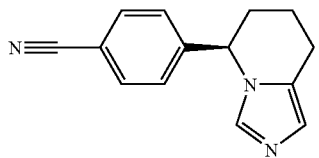

or a pharmaceutically acceptable salt thereof.

A preferred steroidal aldosterone receptor antagonist is eplerenone (cf. EP 122232 A) of the formula

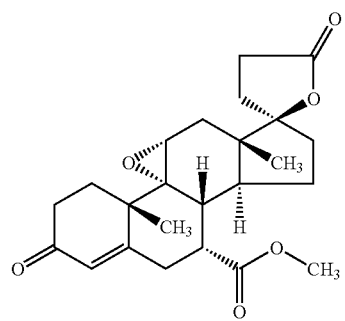

or spironolactone.

Compounds having an inhibitory effects on both angiotensin converting enzyme and neutral endopetidase, so-called dual ACE/NEP inhibitors, can be used for the treatment of cardiovascular pathologies.

A preferred dual angiotensin converting enzyme/neutral endopetidase (ACE/NEP) inhibitor is, for example, omapatrilat (cf. EP 629627), fasidotril or fasidotrilat (cf. EP 419327), or Z 13752A (cf. WO 97/24342) or, if appropriate, a pharmaceutically acceptable salt thereof.

A preferred endothelin antagonist is, for example, bosentan (cf. EP 526708 A), enrasentan (cf. WO 94/25013), atrasentan (cf. WO 96/06095), especially atrasentan hydrochloride, darusentan (cf. EP 785926 A), BMS 193884 (cf. EP 702012 A), sitaxentan (cf. U.S. Pat. No. 5,594,021), especially sitaxsentan sodium, YM 598 (cf. EP 882719 A), S 0139 (cf. WO 97/27314), J 104132 (cf. EP 714897 A or WO 97/37665), furthermore, tezosentan (cf. WO 96/19459), or in each case, a pharmaceutically acceptable salt thereof.

A diuretic is, for example, a thiazide derivative selected from the group consisting of amiloride, chlorothiazide, hydrochlorothiazide, methylchlorothiazide, and chlorothalidon. The most preferred is hydrochlorothiazide.

The structure of the active agents identified by generic or tradenames may be taken from the actual edition of the standard compendium "The Merck Index" or from databases, e.g. LifeCycle Patents lntematonal (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The new compounds of formula (I) or (I A), respectively, may be present for example in the form of pharmaceutical preparations which comprise a therapeutically effective amount of active substance, if necessary together with inorganic or organic, solid or liquid, pharmaceutically acceptable carriers, and which are suitable for enteral, for example oral or parenteral, administration, especially for the prevention and treatment of a condition or disease as described hereinbefore and hereinafter. The present pharmaceutical preparations which, if so desired, may contain further pharmacologically active substances are prepared in a manner known per se, for example by means of conventional mixing, granulating, coating, dissolving or lyophilizing processes, and contain from about 0.1% to 100%, especially from about 1% to about 50%, of the lyophilizates to about 100% of the active substance.

The invention relates likewise to a compound of formula (I) or (I A), respectively, for use in the treatment of the human or animal body.

The invention relates likewise to the use of compounds of formula (I) or (I A), respectively, preferably for the preparation of pharmaceutical compositions, especially for the prevention and treatment of a condition or disease as described hereinbefore and hereinafter.

The invention relates likewise to method for the prevention or treatment of a condition or disease as disclosed hererinbefore and hereinafter comprising administering to a patient (including human) in need thereof an effective amount of a compound of formula (I) or (I A), respectively, or a pharmaceutically acceptable salt thereof.

The dosage may depend on various factors, such as the route of administration, species, age and/or condition of the individual. The daily doses to be administered lie between about 0.25 and about 10 mg/kg in the case of oral administration and preferably between about 20 mg and about 500 mg for warm-blooded animals with a bodyweight of about 70 kg.

The following Examples serve to illustrate the invention; temperatures are given in degrees Celsius.

EXAMPLE 1

2(S),4(S),5(S),7(S)-N-(3-amino-2,2-dimethyl-3-oxo-pronpyl)-2,7-di(1-methylethyl)-4-hydroxy-5-acetylamino-8-[4-methoxy-3-(3-methoxy-propoxy)phenyl]-octanamide 1.35 g of 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide are dissolved inin 6 g of ethanol. A solution of 0.32 g of sodium hydrogencarbonate in 4 ml of water is added. 0.25 g of acetanhydrid are added and the mixture is stirred for an hour. The reaction mixture is extracted with toluene and acetic acid ethyester and the combined extracts are evaporated to dryness. The resulting product

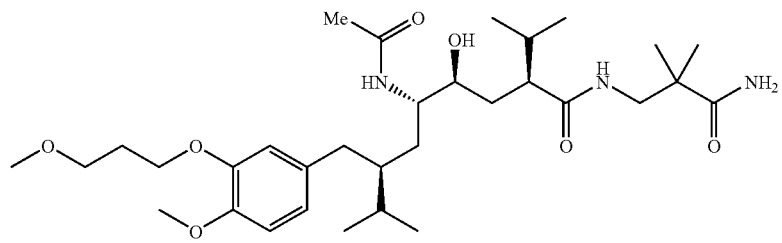

is obtained as amorphous powder.

¹H-NMR (400 MHz, DMSO-$d_6$, numbering according to formula above): 7.45 (m, 2H, N-14-H and N-26-H); 7.15 and 6.73 (2s, 1H each, C-17-NH2); 6.82 (d, 8 Hz, 1H, C-4-H); 6.77 (s, br, 1H, C-1-H); 6.63 (d, 8 Hz, 1H, C-3-H); 4.57 (d, 1H, OH); 3.99 (t, 6 Hz, 2H, C-a-H); 3.88 (br. t, C-9_H); 3.72 (s, 3H, C-f-H); 3.49 (t, 6 Hz, 2H, Ce-H); 3.25 (s, 3H, C-c-H); 3.23 (ABX, 2H, C-15-H); 2.60 (dd, 1H); 2.23 (br. t, 2H); 1.97 (quintett, 2H, C-b-H); 1.88 (s, 3H, C-27-H=Me-CO—N); 1.1–1.75 (several m, 6H); 1.07 (s, 6H; C-18,19-H); 0.88 (3H), 0.86 (3H), 0.76 (6H) (dubletts, 12H, C-20,22,23,25-H).

EXAMPLE 2

α(S),4(S),5(S),2'(S)-N-(3-Amino-2,2-dimethyl-3-oxopropyl)-α-(1-methylethyl)-2-oxo-4-{[2'-(1-methylethyl)-3-(4-methoxy-3-methoxy-propoxy)phenyl]-propyl}-5-oxazolidine-propanamide 0.57 g of 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxy-propoxy)phenyl]-octanamide are added to 10 ml of methylenechloride. At 0° C. 0.16 g of carbonyldiimidazole and 0.01 2 g of N,N-dimethylaminopyridin are added and stirred for 2 days at 0–20° C. The mixture is diluted with methylenchloride and washed three times with 0.5N HCl and once with an aqueous solution of sodium hydrogencarbonate. The organic layer is dried over sodium sulphate, filtered and evaporated to drynes. The resulting compound of formula

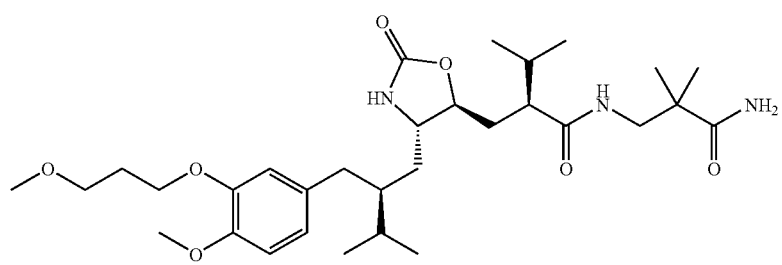

is obtained as colorless powder.

¹H-NMR (400 MHz, DMSO-$d_6$, numbering according to formula above): 7.88 (s, br, 1 H, N-16-H); 7.75 (t, br., 1H, N-16-H); 7.13 and 6.84 (2s, br, 1H each, C-20-NH2); 6.83 (d, 8 Hz, 1H, C-4-H); 6.82 (d, 1.5 Hz, 1H, C-1-H); 6.72 (dd, 8 Hz, 1.5 Hz, 1H, C-3-H); 4.02 (t, 6 Hz, 2H, C-28-H); 3.7–3.75 (br, 1H, C-12-H); 3.73 (s, 3H, C-27-H); 3.50 (t, 6 Hz, 2H, C-30-H); 3.27 (s, 3H, C-31-H); 3.25 (ABX, 2H, C-17-H); 2.45 (ABX, 2H, C-6-H); 1.95 (quintett, 2H, C-29-H); 1.1–1.8 (several m, 6H, C-8-H, C-13-H, C-22-H, C-23-H); 1.05 and 1.07 (2s, 3H each, C-18,19-H); 0.88 (d, 6H) and 0.80 (t, 6H): C-21,23,24,26-H.

What is claimed is:
1. A compound of formula (I)

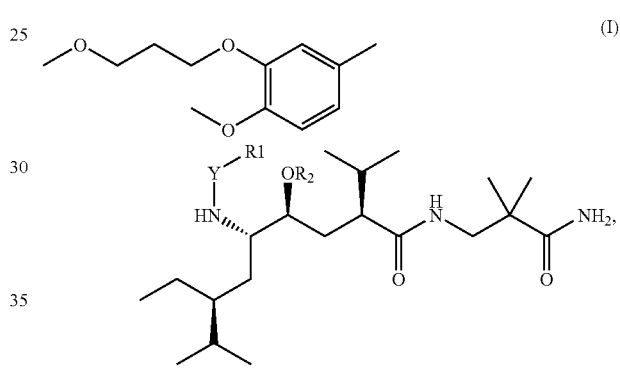

or a pharmaceutically acceptable salt thereof;
wherein Y represents the group —C(=X) or $SO_2$; and
(i) $R_1$ and $R_2$ together form a single bond or methylene; and, if Y represents the group —C(=X), X represents NH, S, or O; or
(ii) $R_1$ represents $C_1$–$C_7$-alkyl; or represents $C_1$–$C_7$-alkyl that is substituted by a substituent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; or represents $C_1$–$C_7$-alkoxy that is unsubstituted or substituted by a substiuent selected from the group consisting of $C_1$–$C_7$-alkyl, $C_1$–$C_7$-alkoxy, hydroxy, halogen, $CF_3$, nitro and cyano; and $R_2$ represents hydrogen; and, if Y represents the group —C(=X), X represents NH, S, or O; or (iii) $R_1$ represents amino; $R_2$ represents hydrogen; and, if Y represents the group —C(=X), X represents NH; or wherein Y represents the group —C(=X); and (iv) $R_1$ and $R_2$ together form a the group —CO—O—; and X represents O.

2. A compound according to claim 1 of formula (I A)

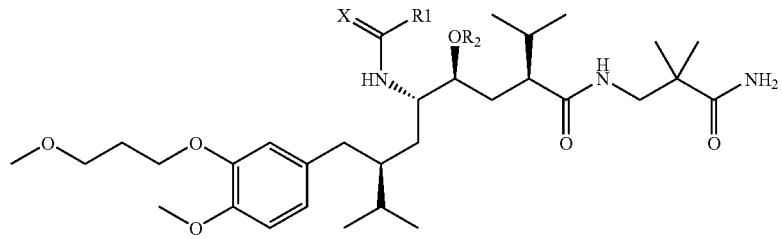

or a pharmaceutically acceptable salt thereof, wherein
(i) $R_1$ and $R_2$ together form a single bond or methylene; and X represents NH, S, or O; or
(ii) $R_1$ represents $C_1$–$C_7$-alkyl; or represents $C_1$–$C_7$-alkyl that is substituted by a substitutent selected from the group consisting of amino, carboxy, hydroxy-$C_1$–$C_7$-alkyl-amino, $C_1$–$C_7$-alkoxy-$C_1$–$C_7$-alkyl-amino, and aryl that is unsubstituted or substituted by a substiuent selected from the group consisting of $C_1$–$C_7$-alkyl, $C_1$–$C_7$-alkoxy, hydroxy, halogen, $CF_3$, nitro and cyano; or represents $C_1$–$C_7$-alkoxy that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano; and $R_2$ represents hydrogen; and X represents NH, S, or O; or
(iii) $R_1$ represents amino; $R_2$ represents hydrogen; and X represents NH.

3. A compound according to claim 2 of formula (I A), wherein $R_1$ and $R_2$ together form a single bond and X is O; or a pharmaceutically acceptable salt thereof.

4. A compound according to claim 2 of formula (I A), wherein $R_1$ represents a residue selected from the group consisting of $C_1$–$C_4$-alkyl, $C_1$–$C_4$-alkoxy or aryl, for example, phenyl that is unsubstituted or substituted by a substiuent selected from the group consisting of $C_1$–$C_7$-alkyl, $C_1$–$C_7$-alkoxy, hydroxy, carboxy, halogen, $CF_3$, nitro and cyano;

$R_2$ is hydrogen; and X is O; or a pharmaceutically acceptable salt thereof; or wherein $R_1$ represents $C_1$–$C_4$-alkyl; $R_2$ is hydrogen; and X is O; or a pharmaceutically acceptable salt thereof.

5. A compound according to claim 2 selected from the group consisting of 2(S),4(S),5(S),7(S)-N-(3-amino-2,2-dimethyl-3-oxopropyl)-2,7-di(1-methylethyl)-4-hydroxy-5-acetylamino-8-[4-methoxy-3-(3-methoxy-propoxy)phenyl]-octanamide and α(S),4(S),5(S),2'(S)-N-(3-Amino-2,2-dimethyl-3-oxopropyl)-α-(1-methylethyl)-2-oxo-4-{[2'-(1-methylethyl)-3-(4-methoxy-3-methoxy-propoxy)phenyl]-propyl}-5-oxazolidine-propanamide or, in each case, a pharmaceutically acceptable salt thereof.

6. A pharmaceutical composition comprising a therapeutically effective amount of a compound according to claim 1 and at least one pharmaceutically acceptable carrier.

7. A pharmaceutical composition comprising a therapeutically effective amount of a compound according to claim 1 and at least one therapeutic agent selected from the group consisting of (i) an $AT_1$-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

8. A pharmaceutical composition comprising a therapeutically effective amount of a compound of claim 2 and at least one pharmaceutically acceptable carrier.

9. A pharmaceutical composition comprising a therapeutically effective amount of a compound according to claim 3 and at least one pharmaceutically acceptable carrier.

10. A pharmaceutical composition comprising a therapeutically effective amount of a compound according to claim 4 and at least one pharmaceutically acceptable carrier.

11. A pharmaceutical composition comprising a therapeutically effective amount of a compound according to claim 5 and at least one pharmaceutically acceptable carrier.

12. A pharmaceutical composition comprising a therapeutically effective amount of a compound according to claim 2 and at least one therapeutic agent selected from the group consisting of (i) an $AT_1$-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

13. A pharmaceutical composition comprising a therapeutically effective amount of a compound according to claim 3 and at least one therapeutic agent selected from the group consisting of (i) an $AT_1$-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

14. A pharmaceutical composition comprising a therapeutically effective amount of a compound according to claim 4 and at least one therapeutic agent selected from the group consisting of (i) an $AT_1$-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

15. A pharmaceutical composition comprising a therapeutically effective amount of a compound according to claim 5 and at least one therapeutic agent selected from the group consisting of (i) an $AT_1$-receptor antagonist or a pharmaceutically acceptable salt thereof, (ii) an angiotensin converting enzyme (ACE) inhibitor or a pharmaceutically acceptable salt thereof, (iii) a beta blocker or a pharmaceutically acceptable salt thereof, (iv) a calcium channel blocker or a pharmaceutically acceptable salt thereof, (v) an aldosterone synthase inhibitor or a pharmaceutically acceptable salt thereof, (vi) an aldosterone receptor antagonist or a pharmaceutically acceptable salt thereof, (vii) a dual angiotensin converting enzyme/neutral endopetidase (ACE/NEP) inhibitor or a pharmaceutically acceptable salt thereof, (viiii) an endothelin receptor antagonist or a pharmaceutically acceptable salt thereof, and (ix) a diuretic or a pharmaceutically acceptable salt thereof.

\* \* \* \* \*